(12) United States Patent
Falgout

(10) Patent No.: US 10,433,566 B1
(45) Date of Patent: Oct. 8, 2019

(54) METHOD FOR INSPECTING SHRIMP

(71) Applicant: Laitram, L.L.C., Harahan, LA (US)

(72) Inventor: Byron M. Falgout, River Ridge, LA (US)

(73) Assignee: Laitram, L.L.C., Harahan, LA (US)

( * ) Notice: Subject to any disclaimer, the term of this patent is extended or adjusted under 35 U.S.C. 154(b) by 0 days.

(21) Appl. No.: 16/163,030

(22) Filed: Oct. 17, 2018

(51) Int. Cl.
*A22C 29/00* (2006.01)
*A22C 29/02* (2006.01)
*A22C 25/04* (2006.01)

(52) U.S. Cl.
CPC .......... *A22C 29/023* (2013.01); *A22C 29/005* (2013.01); *A22C 29/024* (2013.01); *A22C 25/04* (2013.01); *A22C 29/022* (2013.01)

(58) Field of Classification Search
CPC .......... A22C 29/00; A22C 29/05; A22C 29/02; A22C 29/021; A22C 29/022
USPC .......................................................... 452/2
See application file for complete search history.

(56) References Cited

U.S. PATENT DOCUMENTS

| | | | |
|---|---|---|---|
| 6,736,716 B1 * | 5/2004 | Sugiyama | A22C 29/046 452/2 |
| 6,808,448 B1 | 10/2004 | Kanaya et al. | |
| 7,195,551 B2 * | 3/2007 | Shefet | A22C 11/001 426/513 |
| 8,033,898 B2 * | 10/2011 | McNaughton | A23L 3/3526 452/149 |
| 9,930,896 B2 | 4/2018 | Ledet et al. | |

\* cited by examiner

*Primary Examiner* — Richard T Price, Jr.
(74) *Attorney, Agent, or Firm* — James T. Cronvich

(57) ABSTRACT

A method for inspecting peeled shrimp by human operators in a culling station illuminated by ambient visible light and in a dark shell-detection booth illuminated by ultraviolet (UV) lamps. The UV radiation emitted by the lamps is filtered to remove visible light from the filtered UV irradiating the shrimp in the dark booth. Irradiated shrimp shell fluoresces and is detectable by the naked eye. A human operator in the dark booth detects the fluorescing shell and removes those shrimps.

7 Claims, 2 Drawing Sheets

METHOD FOR INSPECTING SHRIMP

BACKGROUND

The invention relates generally to a method for inspecting peeled shrimps.

In the bulk processing of shrimp, automated shrimp peelers remove heads, appendages, and shells from the shrimp. Although the peeling process is generally thorough, some shrimps are left with residual shell. To improve the quality of the final product, shrimps with residual shell are culled from the completely peeled shrimp. Detection of residual shell is often done by visual inspection. But transparent residual shell is not always easy to notice.

SUMMARY

One method embodying features of the invention for inspecting peeled shrimps comprises: (a) providing a dark booth that blocks outside visible light from entering the booth's interior; (b) emitting ultraviolet (UV) radiation directed toward a group of peeled shrimps in the interior of the dark booth; (c) filtering out visible light in the UV radiation to produce filtered UV radiation; (d) irradiating the group of peeled shrimps in the interior of the dark booth with the filtered UV radiation to cause residual shell to fluoresce with visible light; and (e) providing a human operator in the dark booth to visually detect the visible light of fluorescing shell with the naked eye.

DETAILED DESCRIPTION

Figure 1:
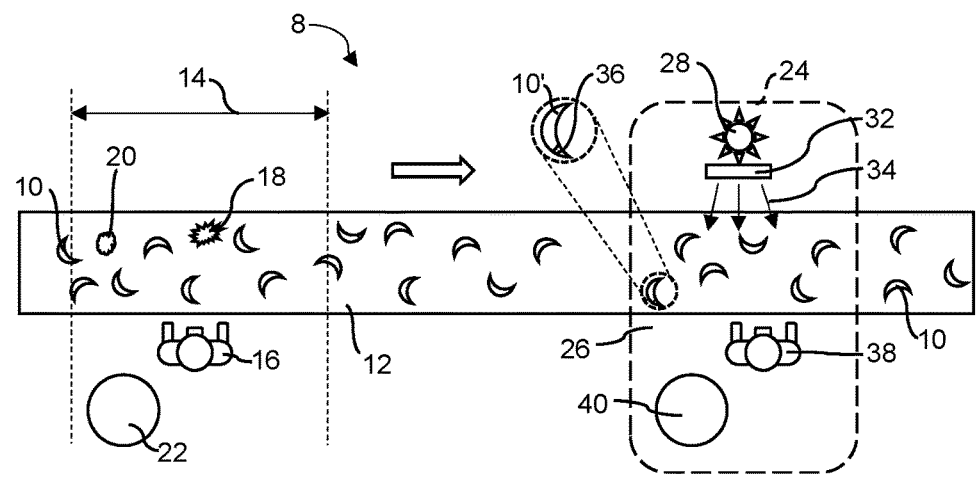
FIG. 1 is a top plan schematic of an inspection system for inspecting peeled shrimp in culling and shell-detection stations embodying features of the invention.

Manual culling and shell-detection stations in a peeled-shrimp inspection system 8 are shown in FIG. 1 in a continuous system. Peeled shrimps 10 loaded onto a conveyor 12, such as a conveyor belt, are conveyed through a culling station 14. A human operator 16 manning the culling station 14 in ambient lighting culls unwanted shrimp bits and debris 18, 20 from the supply of shrimps 10 passing by and deposits the debris 18, 20 in a collection receptacle 22. The conveyor 12, which may be one or more conveyor belts or a water trough, as just two examples, then conveys the peeled shrimps 10 into and through a dark booth 24.

Figure 2:
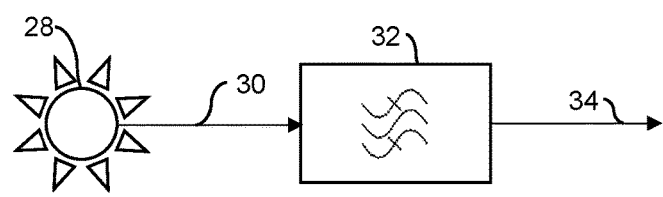
FIG. 2 is a block diagram of a UV source and a filter usable in the shell-detection station of FIG. 1.

The dark booth 24 prevents ambient visible light from entering the booth's interior 26. A UV lamp 28 emits UV radiation 30 directed at the group of shrimps 10 in the booth 24 as also shown in FIG. 2. The UV radiation 30 is filtered by a band-pass filter 32 to filter out visible light and produce filtered UV radiation 34 that irradiates the group of shrimps 10 in the dark booth 24. The filtered UV radiation 34 irradiating the shrimps 10 causes residual shell 36 to fluoresce by shifting some of the UV radiation into the visible-light region of the spectrum. The visible light from the fluorescing shell is visible to the naked human eye and so is detectable by a human operator 38 in the dark booth 24. The human operator 38 in the dark booth removes those shrimps 10' with residual shell 36 from the group of shrimps 10 and deposits them in a reject receptacle 40 from which they can be returned to the peeler. The shrimps 10 exiting the dark booth 24 are free of residual shell.

As an alternative, the dark booth 24 can be operated as a stand-alone quality-control station, in which samples of peeled shrimps are placed on a stationary support surface and inspected by the naked eye of an operator to detect fluorescing shell.

The dark booth 24 blocks enough ambient visible light from entering its interior 26 to ensure that the fluorescence of the shells is detectable by the naked eye. And it has been found that inexpensive UVa lamps, better known as black lights, cause enough fluorescence of the shells to be detectable. Besides being inexpensive, UVa lamps do not subject the human operator 38 in the dark booth 24 to unsafe levels of higher-frequency UV radiation.

Figure 3A:
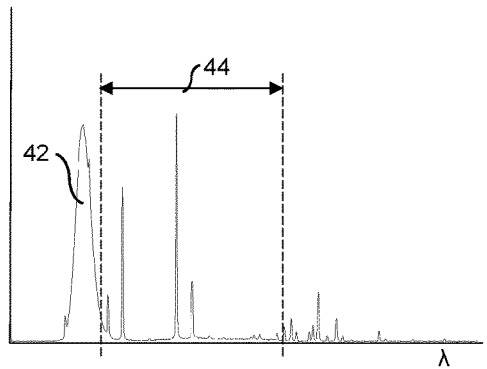
FIG. 3A is the spectrum of the UV radiation emitted by the UV source of FIG. 2.
Figure 3B:
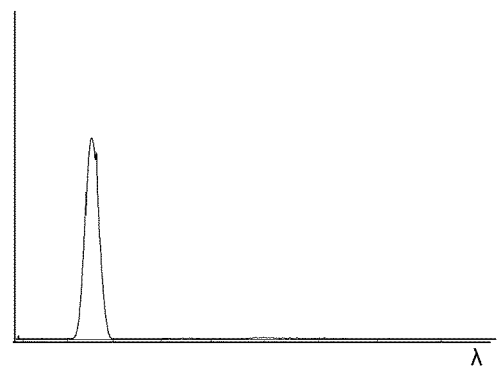
FIG. 3B is the spectrum of the UV radiation of FIG. 3A after passing through a filter blocking visible light.
Figure 4A:
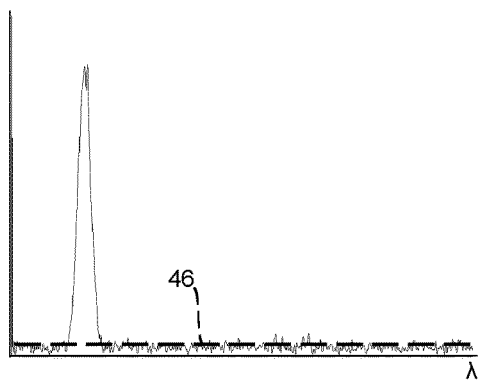
FIG. 4A is the spectrum of the reflected radiation of a completely shelled shrimp.

FIG. 4A shows the spectrum of an unfiltered UVa lamp. The spectrum is shown as a function of wavelength (A) rather than frequency. So, the longer wavelengths and lower frequencies are to the right in the graphs of the spectrum in FIGS. 3A-4B. The unfiltered UVa radiation has a main band concentrated around 350 nm and some longer-wavelength bands in the visible light region of the spectrum. The maximum energy of the UVa lamp in the main band occurs over a range 42 of ultraviolet wavelengths concentrated at about 350 nm just below the visible-light region 44 (about 380 nm to 740 nm). The band-pass filter 32 (FIGS. 1 and 2) filters out the visible light above about 400 nm, as well as shorter-wavelength radiation below about 310 nm, as shown in the spectrum of the filtered UVa radiation in FIG. 3B to make the fluorescence of shell easier to see. The filter also affects the spectrum of the main UVa lamp energy 42 with its peak at about 350 nm by shifting the spectral peak of the filtered UVa irradiating the shrimps to about 365 nm.

Figure 4B:
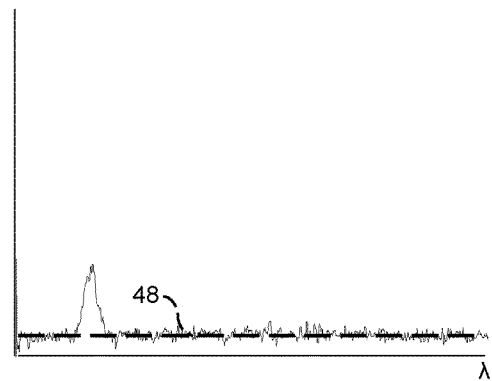
FIG. 4B is the spectrum of the reflected radiation of shrimp shell.

FIG. 4A shows the spectrum of reflected radiation from completely shelled shrimps irradiated by the filtered UVa radiation of FIG. 3B. FIG. 4B shows the spectrum of reflected radiation from shell irradiated by the filtered UVa radiation of FIG. 3B. The level 46 of the reflected radiation in the visible light region for completely shelled shrimp is lower than the level 48 of the reflected and fluorescent radiation from fluorescing shell, which is detectable by the naked eye in the dark booth. The peak energy of the main band of reflected UVa radiation from shrimp shell as shown in FIG. 4B is much lower than the reflected UVa radiation from completely shelled shrimps as shown in FIG. 4A indicating that much of the main band of incident UVa energy is absorbed by the shell and converted into higher-wavelength fluorescent light easily visible to the naked eye.

What is claimed is:

1. A method for inspecting peeled shrimps comprising:
   providing a dark booth blocking outside visible light from entering the interior of the dark booth;
   emitting UV radiation directed toward a group of peeled shrimps in the interior of the dark booth;
   filtering out visible light in the UV radiation to produce filtered UV radiation;
   irradiating the group of peeled shrimps in the interior of the dark booth with the filtered UV radiation to cause residual shell on the peeled shrimps to fluoresce with visible light;

providing a human operator in the dark booth to visually detect the visible light of fluorescing shell with the naked eye.

2. The method as claimed in claim 1 wherein the human operator removes peeled shrimps with residual shell from the group of peeled shrimps in the dark booth.

3. The method as claimed in claim 1 comprising conveying peeled shrimps through the interior of the dark booth on a conveyor belt.

4. The method as claimed in claim 1 comprising conveying peeled shrimps through the interior of the dark booth in a water trough.

5. The method as claimed in claim 1 comprising supporting the group of peeled shrimps in the interior of the dark booth on a stationary support surface.

6. The method as claimed in claim 1 wherein the UV radiation is UVa radiation.

7. The method as claimed in claim 1 comprising a culling station outside the dark booth wherein unwanted shrimp parts and other debris are visually detected by human eye under ambient visible light and manually removed from peeled shrimps before the peeled shrimps enter the dark booth.

\* \* \* \* \*